US012514963B2

(12) United States Patent
Fallman et al.

(10) Patent No.: US 12,514,963 B2
(45) Date of Patent: Jan. 6, 2026

(54) INLINE HEATER OVERHEATING SYSTEM AND METHOD

(71) Applicants: BAXTER INTERNATIONAL INC., Deerfield, IL (US); BAXTER HEALTHCARE SA, Glattpark (CH)

(72) Inventors: Oskar Erik Frode Styrbjorn Fallman, Lund (SE); Michael Pettersson, Malmo (SE); Jimmie Marcus Axel Hansson, Limhamn (SE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 380 days.

(21) Appl. No.: 17/903,366

(22) Filed: Sep. 6, 2022

(65) Prior Publication Data

US 2023/0070999 A1 Mar. 9, 2023

Related U.S. Application Data

(60) Provisional application No. 63/241,738, filed on Sep. 8, 2021.

(51) Int. Cl.

*A61M 1/16* (2006.01)
*A61M 1/28* (2006.01)
*H05B 3/00* (2006.01)

(52) U.S. Cl.

CPC ................ *A61M 1/16* (2013.01); *A61M 1/28* (2013.01); *H05B 3/0085* (2013.01); *A61M 2205/3334* (2013.01)

(58) Field of Classification Search

CPC .. A61M 1/16; A61M 1/28; A61M 2205/3334; A61M 1/1686;

(Continued)

(56) References Cited

U.S. PATENT DOCUMENTS

2008/0021377 A1* 1/2008 Kienman .............. A61M 1/153 604/29
2008/0105600 A1* 5/2008 Connell .............. A61M 1/1664 210/85

(Continued)

FOREIGN PATENT DOCUMENTS

CN 103037914 A * 4/2013 ........... A61B 5/4288
CN 210373383 U * 4/2020 .............. F22B 35/18
WO WO-2010105918 A1 * 9/2010 .............. F16L 25/01

OTHER PUBLICATIONS

PE2E Search English translation of WO 2010105918A1, published Sep. 23, 2010. (Year: 2010).*

(Continued)

*Primary Examiner* — Joseph W Drodge
(74) *Attorney, Agent, or Firm* — K&L Gates LLP

(57) ABSTRACT

An inline heating system including an inline heater including a heater element; a control unit configured to cause one of voltage or current to be applied to power the inline heater; and a current or voltage meter positioned and arranged to measure the other of current or voltage at the heater element due to the applied voltage or current, wherein the control unit is further configured to determine a heater element resistance using the applied voltage or current and the measured current or voltage as part of a no flow or low flow condition detection algorithm implemented by the control unit, wherein the voltage or current applied to power the inline heater is stopped if the no flow or low flow condition is detected.

15 Claims, 3 Drawing Sheets

(58) Field of Classification Search
CPC ...... A61M 2205/18; A61M 2205/3368; A61M 2205/3653; A61M 2205/70; A61M 1/166; A61M 1/1664; A61M 5/44; A61M 2205/33; A61M 2205/3379; A61M 2205/36; H05B 1/025; H05B 3/0004; H05B 3/0019; H05B 3/0023; H05B 3/0085; H05B 2203/014; H05B 2203/021; H05B 2203/035
USPC ................. 219/108–110, 260, 262, 268, 269
See application file for complete search history.

(56) References Cited

U.S. PATENT DOCUMENTS

| | | | | |
|---|---|---|---|---|
| 2016/0082173 | A1* | 3/2016 | Coll | A61M 1/155 604/114 |
| 2017/0028159 | A1* | 2/2017 | Ghalib | A61M 16/0051 |
| 2019/0316948 | A1* | 10/2019 | Karol | G16H 40/63 |
| 2020/0329533 | A1* | 10/2020 | Wallinger | H05B 3/0019 |

OTHER PUBLICATIONS

Escapenet English translation of WO 2010105918A1, published Sep. 23, 2010. (Year: 2010).*
PE2E Search English translation of CN103037914A, published Apr. 10, 2013. (Year: 2013).*
PE2E English Translation of Publication CN 210373383, published Apr. 21, 2020. (Year: 2020).*

* cited by examiner

INLINE HEATER OVERHEATING SYSTEM AND METHOD

PRIORITY CLAIM

The present application claims priority to and the benefit of U.S. Provisional Patent Application No. 63/241,738, filed on Sep. 8, 2021, the entire contents of which are hereby incorporated

BACKGROUND

The present disclosure relates generally to medical fluid treatments and in particular to the heating of treatment fluid during dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid or PD fluid, into a patient's peritoneal chamber via a catheter. The PD fluid comes into contact with the peritoneal membrane in the patient's peritoneal chamber. Waste, toxins and excess water pass from the patient's bloodstream, through the capillaries in the peritoneal membrane, and into the PD fluid due to diffusion and osmosis, i.e., an osmotic gradient occurs across the membrane. An osmotic agent in the PD fluid provides the osmotic gradient. Used PD fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used PD fluid to drain from the patient's peritoneal cavity. The patient then switches fluid communication so that the patient catheter communicates with a bag of fresh PD fluid to infuse the fresh PD fluid through the catheter and into the patient. The patient disconnects the catheter from the fresh PD fluid bag and allows the PD fluid to dwell within the patient's peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

APD is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh PD fluid and to a fluid drain. APD machines pump fresh PD fluid from a dialysis fluid source, through the catheter and into the patient's peritoneal chamber. APD machines also allow for the PD fluid to dwell within the chamber and for the transfer of waste, toxins and excess water to take place. The source may include multiple liters of dialysis fluid, including several solution bags.

APD machines pump used PD fluid from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Dialysis fluid or treatment for HD, HF, HDF and PD is typically heated prior to being delivered to a dialyzer (HD, HDF), blood line (HF, HDF) or the patient (PD). The dialysis fluid is typically heated to body temperature or 37° C. so that the patient does not experience a thermal shock when the dialysis fluid comingles with the patient's blood or is delivered to the patient's peritoneal cavity. One type of dialysis fluid heater is an inline dialysis fluid heater, which heats the dialysis fluid as it passes through the inline heater. Inline heaters are advantageous because they operate online as treatment is taking place and do not require a separate amount of time offline from the treatment. One drawback to online heating however is that if there is no dialysis fluid flowing when the inline heater is powered, the inline heater may overheat.

There is accordingly a need for an effective, low cost way of preventing or mitigating overheating in an inline heater due to a no or low flow condition.

SUMMARY

The present disclosure involves the use of an inline heater in a dialysis machine, which may be any type of dialysis machine, such as a peritoneal dialysis ("PD") machine, hemodialysis ("HD") machine, hemofiltration ("HF") machine, hemodiafiltration ("HDF") machine or continuous renal replacement therapy ("CRRT") machine. The inline heater heats dialysis fluid as it flows through the heater towards the patient (PD), dialyzer (HD, HDF), or blood line (HF, HDF, CRRT) for treatment. The inline heating method is opposed to a batch heater commonly used with PD for heating a bag of dialysis fluid prior to being delivered for treatment. The inline heater of the present disclosure is advantageous because it does not require the footprint involved with maintaining a bag for batch heating. The inline heater also heats the dialysis fluid as it is needed, eliminating the need for a heating period prior to beginning treatment.

The inline heater of the present disclosure is disadvantageous from one standpoint in that if it is attempted to heat dialysis fluid while no dialysis fluid is flowing, the inline heater can overheat. A flow switch may be placed ahead of the inline heater to make sure that flow is present as a condition for energizing the heater. Flow switches add cost however and can become stuck or otherwise not function properly.

The inline fluid heating system of the present solution involves determining the resistance of the heater element of the inline heater. The resistance of the heater element increases in a typical manner with an increase in temperature. The resistance of the heater element is one embodiment calculated by knowing an amount of voltage or current applied to the heater element and measuring the other of the current or voltage at the heater element while the inline heater is being powered. Heater element resistance $R_e$ is then equal to $V_e/I_e$. The calculated resistance is applied to an algorithm stored in a control unit of the dialysis machine to determine if a low flow or no flow condition within the inline heater exists.

One possible algorithm sets a maximum heater element resistance increase or resistance derivate (change in heater element resistance over time). By looking at heater element resistance rate of change or increase, a no or low flow condition through the inline heater may be detected early before the temperature increases too much or to a point that could damage the inline heater. When there is no fluid flow in the energized inline heater, the temperature increases rapidly and hence the heater resistance increases rapidly. If the change in heater element resistance over a period or of time (rate of change), e.g., a sample period meets or exceeds a set maximum rate of change of resistance per the period of time, the algorithm triggers the control unit to automatically deenergize the inline heater, stop treatment, and alarm the patient, caregiver or nurse.

One possible implementation of the overheating algorithm is to run a characterizing program that characterizes the inline heater at the time of manufacture and/or servicing of the dialysis machine. The characterizing program characterises how the inline heater resistance relates to temperature. Here, the inline heater is energized while receiving a known flowrate of fluid. Input power is varied while the flowrate is held constant. A temperature sensor may be used to measure the test fluid temperature downstream from the inline heater to confirm that the heater is heating the test fluid properly. The characterising program enables measured heater element resistances (correlated with heater element temperature) to be known for a given fluid flowrate and over a common or use range of input power settings. A resulting calibration data table is then stored in the memory of the control unit of the dialysis machine. The control unit uses the calibration data during treatment to detect when the inline heater is overheating, that is, to detect for a given or commanded flowrate and a commanded input power setting, that the measured heater element resistance $R_e$ is greater than it should be for the commanded dialysis fluid temperature.

The algorithm stored in the control unit of the dialysis machine may accordingly analyze two factors (i) rate of change in heater element resistance (derivative) indicating that a no or low flow condition is beginning and (ii) the determine resistance compared to the calibration resistance. That is, the rate of change in heater element resistance may be high, indicating that a no or low flow condition may be beginning, but if the determined heater element resistance (and corresponding temperature) is lower than what the calibration data says the heater element resistance should be for a given flowrate and power input setting, then the algorithm allows the control unit of the dialysis machine to continue treatment.

In an embodiment, the cycle rate for the current or voltage measurement may be very high and noisy, and thus the algorithm may be configured in an embodiment to take many measurements, e.g., over the period of a second or more, before making a no or low flow determination, deenergizing the inline heater, stopping treatment, and alarming the patient, caregiver or nurse. Taking many measurements over a safe time period that is too short for the inline heater to overheat significantly helps to prevent false trips. Taking many measurements also provides an adequate number of samples to efficiently supress measurement signal noise.

An analog heater protection circuit may be provided as part of the control unit of the present system to detect the rate of change or derivative, discussed herein, in either one or both of current and/or voltage. The analog heater protection circuit may include one or more of measurement circuitry, divider circuitry, a differential circuit, a comparator, and/or a lowpass/timer circuit.

In light of the disclosure set forth herein, and without limiting the disclosure in any way, in a first aspect, which may be combined with any other aspect, or portion thereof, an inline heating system includes an inline heater including a heater element; a control unit configured to cause one of voltage or current to be applied to power the inline heater; and at least one of a current or voltage meter outputting to the control unit and arranged to measure at least one of the current or voltage at the heater element due to the applied voltage or current, wherein the control unit is further configured to determine a heater element resistance using the applied voltage or current and the measured at least one of the current or voltage as part of a no flow or low flow condition detection algorithm implemented by the control unit, wherein the voltage or current applied to power the inline heater is stopped if the no flow or low flow condition is detected.

In a second aspect, which may be combined with any other aspect, or portion thereof, the control unit includes the at least one of the current or voltage meter.

In a third aspect, which may be combined with any other aspect, or portion thereof, the control unit is configured to determine multiple heater element resistances using the applied voltage or current and the measured at least one current or voltage at different times over a sample period to determine if the no flow or low flow condition is detected.

In a fourth aspect, which may be combined with any other aspect, or portion thereof, the heater element is a first heater element, and which includes at least one additional heater element, wherein the control unit is configured to determine a heater element resistance for each heater element as part of the no flow or low flow condition detection algorithm.

In a fifth aspect, which may be combined with any other aspect, or portion thereof, the at least one current or voltage meter is a first current or voltage meter, and which includes at least one additional current or voltage meter arranged to measure the at least one current or voltage at the at least one additional heater element.

In a sixth aspect, which may be combined with any other aspect, or portion thereof, the control unit is configured to stop the voltage or current applied to power the inline heater if the no flow or low flow condition is detected at any of the heater elements.

In a seventh aspect, which may be combined with any other aspect, or portion thereof, the control unit is configured to compare a rate of change in determined heater element resistance to a set maximum rate of change in determined heater element resistance as part of the low flow condition detection algorithm implemented by the control unit.

In an eighth aspect, which may be combined with any other aspect, or portion thereof, the rate of change in determined heater element resistance is a positive rate of change.

In a ninth aspect, which may be combined with any other aspect, or portion thereof, the control unit is configured to compare the determined heater element resistance to a calibrated heater element resistance as part of the low flow condition detection algorithm implemented by the control unit.

In a tenth aspect, which may be combined with any other aspect, or portion thereof, the calibrated heater element resistance is determined remote from the inline heating system and then stored in the control unit.

In an eleventh aspect, which may be combined with any other aspect, or portion thereof, the calibrated heater element resistance is specific to at least one of (i) fluid flowrate through the inline heater or (ii) input power to the inline heater.

In a twelfth aspect, which may be combined with any other aspect, or portion thereof, the control unit is configured to measure the at least one of the current or voltage at a sample rate that is of at least one of (i) 100 Hz or greater or (ii) at least two times greater than a frequency of a pulsed voltage source powering the inline heater.

In a thirteenth aspect, which may be combined with any other aspect, or portion thereof, the control unit includes an analog heater protection circuit configured to filter the measured at least one of the current or voltage.

In a fourteenth aspect, which may be combined with any other aspect, or portion thereof, an inline heating system includes an inline heater including a heater element; a voltage source or a current source positioned to apply a voltage or current to power the inline heater; and an analog heater protection circuit configured to (i) measure at least one of the current or voltage at the heater element due to the applied voltage or current, (ii) determine a heater element resistance using the applied voltage or current and the measured at least one of the current or voltage, and (iii) provide a stop power signal if the inline heater element resistance indicates a no flow or low flow condition.

In a fifteenth aspect, which may be combined with any other aspect, or portion thereof, the analog heater protection circuit includes at least one of: measurement circuitry, divider circuitry, a differential circuit, a comparator, or a lowpass/timer circuit.

In a sixteenth aspect, which may be combined with any other aspect, or portion thereof, an inline heating system includes an inline heater including a heater element; and a control unit configured to compare a rate of change in heater element resistance to a set maximum rate of change in heater element resistance as part of a no flow or low flow condition detection algorithm implemented by the control unit, wherein power applied to the inline heater is stopped if the no flow or low flow condition is detected.

In a seventeenth aspect, which may be combined with any other aspect, or portion thereof, the control unit is further configured to compare at least one determined heater element resistance to at least one calibrated heater element resistance as part of the low flow condition detection algorithm implemented by the control unit.

In an eighteenth aspect, which may be combined with any other aspect, or portion thereof, the at least one calibrated heater element resistance is determined remote from the inline heating system and then stored in the control unit.

In a nineteenth aspect, which may be combined with any other aspect, or portion thereof, the at least one calibrated heater element resistance is specific to at least one of (i) fluid flowrate through the inline heater or (ii) input power to the inline heater.

In a twentieth aspect, which may be combined with any other aspect, or portion thereof, the inline heating system is provided as part of a peritoneal dialysis machine, hemodialysis machine, hemofiltration machine, hemodiafiltration machine, continuous renal replacement therapy machine, water purification unit, dialysis fluid preparation unit, or blood warmer.

In a twenty-first aspect, which may be combined with any other aspect, or portion thereof, any of the features, functionality and alternatives described in connection with any one or more of FIGS. 1 to 4 may be combined with any of the features, functionality and alternatives described in connection with any other of FIGS. 1 to 4.

In light of the above aspects and the present disclosure, it is accordingly an advantage of the present disclosure to provide a dialysis machine having an inline heater that is deenergized upon a no or low flow condition.

It is another advantage of the present disclosure to provide a dialysis machine having cost effective inline heater no or low flow protection.

It is a further advantage of the present disclosure to provide a dialysis machine having inline heater no or low flow protection that does not require significant additional hardware.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
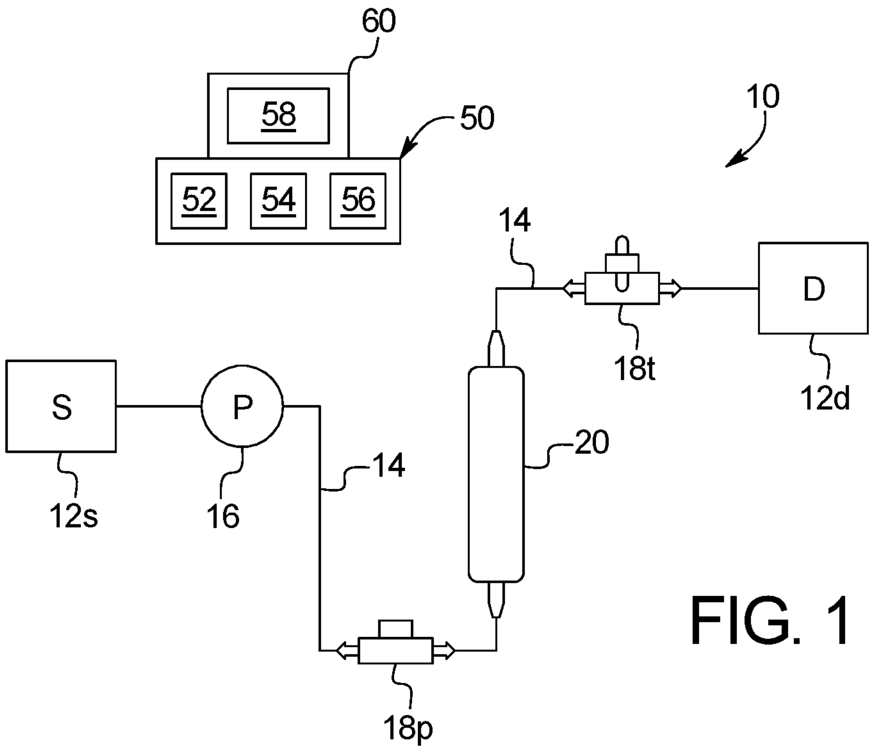
FIG. 1 is a schematic flow diagram illustrating an inline heater in combination with a pump, pressure sensor and temperature sensor, which may be used in many different types of dialysis modalities, such as peritoneal dialysis ("PD"), hemodialysis ("HD") machine, hemofiltration ("HF"), hemodiafiltration ("HDF"), continuous renal replacement therapy ("CRRT") and blood warming.

Referring now to the drawings and in particular to FIG. 1, an inline heating system 10 is illustrated. Inline heating system 10 may be used in many medical fluid applications including but not limited to peritoneal dialysis ("PD"), hemodialysis ("HD") machine, hemofiltration ("HF"), hemodiafiltration ("HDF"), continuous renal replacement therapy ("CRRT") and blood warming. While dialysis is a primary focus for inline heating system 10, the system is not limited to same. For example inline heating system 10 may be employed in a water purification unit that prepares purified water for the creation of dialysis fluid, and which heats the water either for downstream use or for disinfection. Inline heating system 10 may be employed alternatively in a dialysis fluid preparation unit that prepares dialysis fluid online, and which heats the dialysis fluid for downstream use or for disinfection.

Inline heating system 10 includes a fluid source 12*s*, which may be a PD fluid source, HD fluid source, replacement fluid source (HF, HDF, CRRT), or water source for example. Inline heating system 10 includes a fluid destination 12*d*, which may be the patient's peritoneal cavity (PD), a dialyzer (HD, HDF), a blood line (HF, HDF, CRRT), a dialysis fluid preparation unit if inline heating system 10 is employed in or provided by a water purification unit, or a dialysis machine (e.g., PD cycler) if dialysis inline heating system 10 is employed in or provided by a dialysis fluid preparation unit. Fluid source 12*s* and fluid destination 12*d* may alternatively both be the patient when inline heating system 10 is provided as part of a blood warmer.

Fluid from source 12*s* (which will hereafter be termed dialysis fluid even though the fluid is not limited to same as discussed above) is pumped along a fluid line 14 via a pump 16. Pump 16 may be any type of fluid pump, e.g., a durable (reusable) pump that contacts the dialysis fluid directly, such as a piston, gear, centrifugal or rotary vane pump. Pump 16 may alternatively have a disposable component, such as a pneumatic pump operating with a disposable cassette, an electromechanical pump operating with a disposable cassette, or a peristaltic pump operating with a peristaltic tubing segment.

It is contemplated that there be many different components located along fluid line 14 between fluid source 12*s* and fluid destination 12*d*, such as one or more valve, air trap and various sensors. For ease of illustration inline heating system 10 is shown having a pressure sensor 18*p* and a temperature sensor 18*t*. The output of pressure sensor 18*p* may be used as feedback for controlling pump 16 so as not to exceed a positive or negative pressure limit. The output of the temperature sensor 18*t* may be used as feedback for controlling the input power to inline heater 20. Temperature sensor 18*t* is located downstream from inline heater 20 so as to sense the temperature of the dialysis fluid exiting the heater. If desired, an additional temperature sensor may be located upstream of inline heater 20 to provide feedforward information concerning the temperature of dialysis fluid entering inline heater 20.

FIG. 1 further illustrates that inline heating system 10 of the present disclosure includes a control unit 50, which may be the control unit of a dialysis machine (e.g., PD cycler), water purification unit or a dialysis fluid preparation unit. Control unit 50 in the illustrated embodiment includes one or more processor 52, one or more memory 54 and a video controller 58. Control unit 50 receives, stores and processes signals or outputs from pressure sensor 18*p*, temperature sensor 18*t* and other sensors provided by the machine or unit, such as a conductivity sensor (not illustrated). Control unit 50 uses pressure feedback from pressure sensor 18*p* to control pump 16 to pump dialysis fluid at a desired pressure or within a safe pressure limit (e.g., within 0.21 bar (three psig) of positive pressure to a patient's peritoneal cavity). Control unit 50 uses temperature feedback from temperature sensor 18*t* to control inline heater 20 to heat the dialysis fluid to a desired temperature, e.g., body temperature or 37° C.

Video controller 58 of control unit 50 interfaces with a user interface 60 of the machine or unit, which may include a display screen operating with a touchscreen and/or one or more electromechanical button, such as a membrane switch. User interface 60 may also include one or more speaker for outputting alarms, alerts and/or voice guidance commands. User interface 60 may be provided with the machine or unit as illustrated in FIG. 1 and/or be a remote user interface operating with control unit 50. Control unit 50 may also include a transceiver (not illustrated) and a wired or wireless connection to a network, e.g., the internet, for sending treatment data to and receiving prescription instructions from a doctor's or clinician's server interfacing with a doctor's or clinician's computer.

Figure 2:
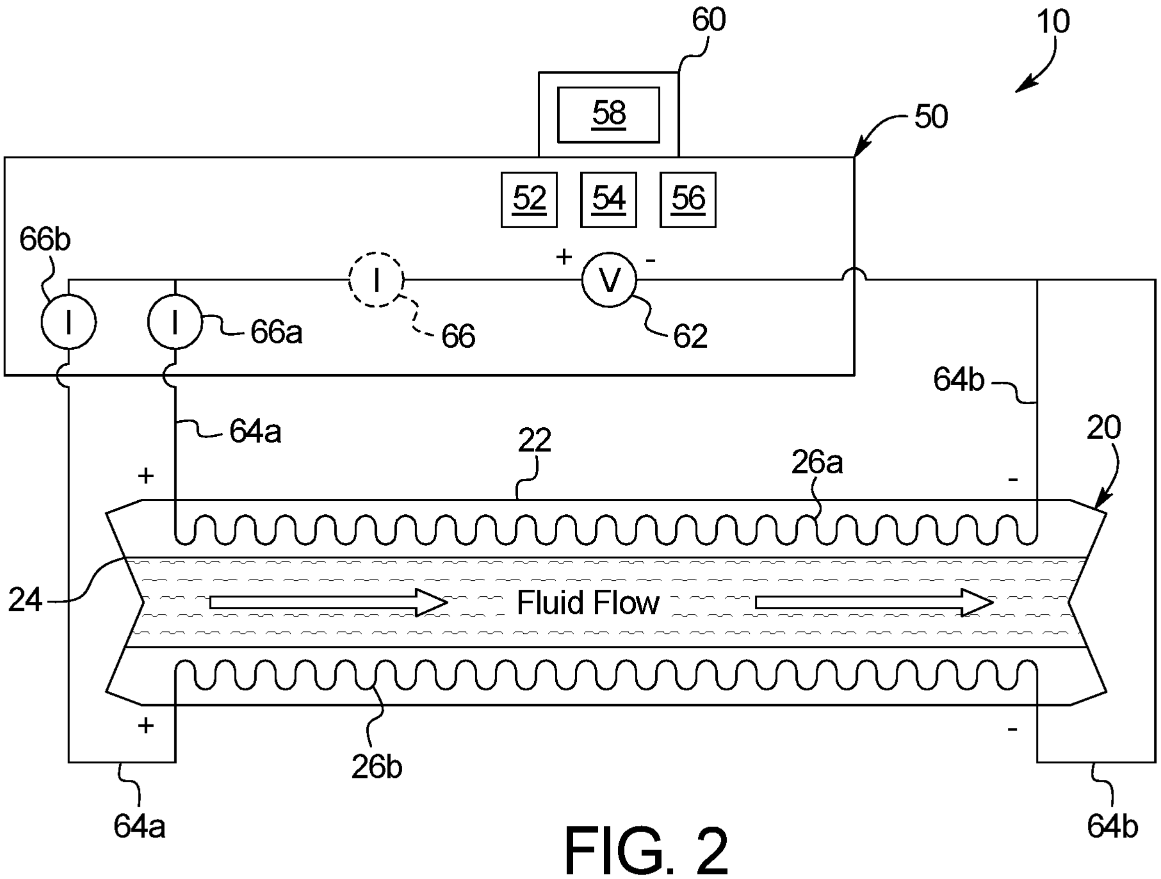
FIG. 2 is a sectioned view of the inline heater of FIG. 1 illustrating multiple heater elements and sensing components used for the low or no flow detection of the present disclosure.

Referring now to FIG. 2, inline heater 20 is illustrated in more detail. In the illustrated embodiment, inline heater 20 includes a housing 22 that surrounds a fluid heating pathway 24. Pathway 24 is illustrated as being straight for ease of illustration but may have alternative shapes, such as a coiled or serpentine shape. Also, while inline heater 20 is illustrated as a durable component that does not operate with a disposable unit, inline heater 20 may alternatively operate with a fluid carrying disposable unit, such as a disposable unit defining a coiled or serpentine heating pathway.

Inline heater 20 in the illustrated embodiment includes a plurality of heater elements 26*a*, 26*b*, such as two heater elements. Inline heater 20 may alternatively include only a single heater element or more than two heater elements 26*a*, 26*b*. Heater elements 26*a*, 26*b* in the illustrated embodiment are located between housing 22 and fluid heating pathway 24, on the inside of housing 22 and on the outside of fluid heating pathway 24. Inline heater 20 may be configured differently however. For example, heater elements 26*a*, 26*b* may instead be located along the center of housing 22. Fluid heating pathway 24 here extends around the outside of the centrally located heater elements 26*a*, 26*b*, between the heater elements and housing 22, which in any heater embodiment may be thermally insulated. Control unit 50, for any configuration of inline heater 20, controls the power provided to heater elements 26*a*, 26*b*. Control unit 50 may do so by controlling either the voltage or current to heater elements 26*a*, 26*b*. The more voltage or current supplied, the more power is provided to inline heater 20, and thus more heating of dialysis fluid flowing through inline heater 20 takes place, resulting in a higher dialysis fluid temperature.

In the illustrated embodiment, control unit 50 controls the voltage from a voltage source 62 to each heater element 26*a*, 26*b*. Voltage source 62 may be a 90 to 130 VAC, a 200 to 240 VAC voltage source, or a voltage source supplying direct current voltage to heater element 26*a*, 26*b*. A positive voltage source line 64*a* extends to one end of each heater element 26*a*, 26*b*, while a negative voltage source line 64*b* extends to the other end of each heater element 26*a*, 26*b*.

Control unit 50 in the illustrated embodiment also includes current meters 66*a*, 66*b* for heater elements 26*a*, 26*b*, respectively. Current meters 66*a*, 66*b* are connected in series with heater elements 26*a*, 26*b* to be able to measure the current applied to each heater element. In the illustrated embodiment, current meters 66*a*, 66*b* are located along positive voltage source lines 64*a* extending to one end of each heater element 26*a*, 26*b*. In an alternative embodiment shown in dashed line, a single current meter 66 may be used to read the current flowing through multiple heater elements 26*a* and 26*b*, wherein control unit 50 may index or switch through readings from each heater element in a cyclical manner. Control unit 50 may alternatively operate with single current meter 66 so as to read both currents (through lines 64*a* and 64*b*) along the common line having single sensor 66. Here, it is not required to cycle sensor 66 to read the different lines 64*a*, 64*b* individually.

It is contemplated for control unit 50 to instead measure both voltage and current simultaneously to obtain good accuracy for the resistance value $R_e$ of each heater element 26*a*, 26*b*. As discussed below in connection with FIG. 3, an analog heater protection circuit may be provided with control unit 50 to detect the rate of change or derivative, discussed herein, in either one or both of current and/or voltage.

Inline heater 20 of inline heating system 10 is disadvantageous from one standpoint in that if it is attempted to heat dialysis fluid while no dialysis fluid is flowing, inline heater 20 can overheat. A flow switch may be placed ahead of inline heater 20 to make sure that flow is present as a condition for control unit 50 to energize the heater. Flow switches add cost however and can become stuck or otherwise not function properly.

Inline heating system 10 solves the overheating problem by configuring control unit 50 to determine the resistance $R_e$ of each heater element 26*a*, 26*b* of inline heater 26. The resistance $R_e$ of each heater element 26*a*, 26*b* increases in a typical manner upon an increase in temperature. The resistance $R_e$ of each heater element 26*a*, 26*b* is in one embodiment calculated by knowing an amount of voltage or current applied to each heater element 26*a*, 26*b* (in FIG. 2 voltage $V_e$ to the heater elements is controlled by control unit 50) and measuring the other of the current or voltage in each heater element 26*a*, 26*b* (in FIG. 2 current $I_e$ along heater elements 26*a*, 26*b* is measured by control unit 50) while inline heater 20 is being powered. Heater element resistance $R_e$ is then equal to $V_e/I_e$. The calculated resistance is applied to an algorithm stored in memory 54 of control unit 50, which is interrogated by processor 52 to determine if a low flow or no flow condition within inline heater 20 exists.

Figure 3:
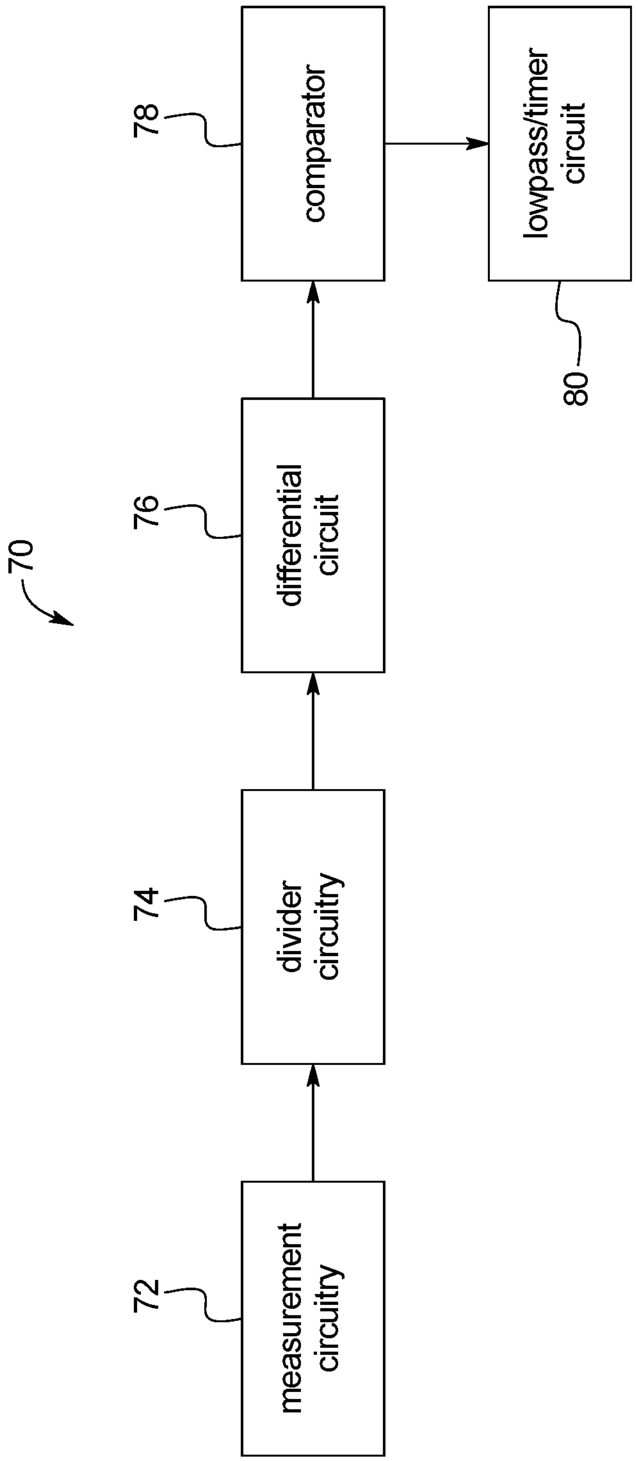
FIG. 3 is a schematic block diagram illustrating an alternative embodiment for the system of the present disclosure, which uses an analog heater protection circuit.

Referring now to FIG. 3, in an alternative embodiment, system 10 of the present disclosure may employ an analog heater protection circuit 70, which performs some or all of the functionality described above as being performed via software using one or more processor 52 and one or more memory 54. It should be appreciated that control unit 50 as discussed herein also includes analog heater protection circuit 70 and any other heater protection circuitry that may be employed by system 10. Control unit 50 includes all supervisory control side and protective side hardware and software and all lower level hardware (including heater protection circuit 70) and software.

As illustrated in FIG. 3, analog heater protection circuit 70 may include measurement circuitry 72, which takes measurements $V_e$ and $I_e$. Circuitry 72 may include a current probe, e.g., an ACS723 current probe, which measures the current $I_e$. Measurement circuitry 72 may include a suitably sized resistor grid to measure the voltage $V_e$. Measurement circuitry 72 may also include a low pass filter that filters two voltage signals (one representing current $I_e$ and the other representing voltage $V_e$). A standard RC lowpass filter, for example, may be used to suppress the most prevalent noise created by the pulsed controller. The two voltage signals (possibly filtered) are fed from measurement circuitry 72 to divider circuitry 74, which includes a divider, e.g., an AD538 divider, creating a new voltage corresponding to heater element resistance $R_e$.

The voltage corresponding to heater element resistance $R_e$ is fed from divider circuitry 74 to a differential circuit 76 that creates a second new voltage representing a rate of change of heater element resistance $R_e$. Differential circuit 76 may be (i) a passive capacitive differential circuit that includes a capacitor and resistor, (ii) a passive inductive differential circuit that includes an inductor and a resistor, or (iii) an active differential circuit, which may also include a capacitor and a resistor as well as an operation amplifier. The second new voltage representing the rate of change of heater element resistance $R_e$ is then delivered from differential circuit 76 to a comparator 78, the output of which may be used to disable or to turn off inline heater 20 if the rate of change of heater element resistance $R_e$ meets or exceeds a threshold rate of change of heater element resistance $R_e$ set at comparator 78. A lowpass/timer circuit 80 may be provided after comparator 78 to remove potential glitches/disturbances. Lowpass/timer circuit 80 ensures that the no/low flow signal does not go high based on noise that may have gotten through to the lowpass filter/timer circuit. Lowpass/timer circuit 80 instead ensures that the signal is stable/triggered for a certain amount of time and that inline heater 20 is not depowered or shut off for small signal spikes or noises that may occur.

Figure 4:
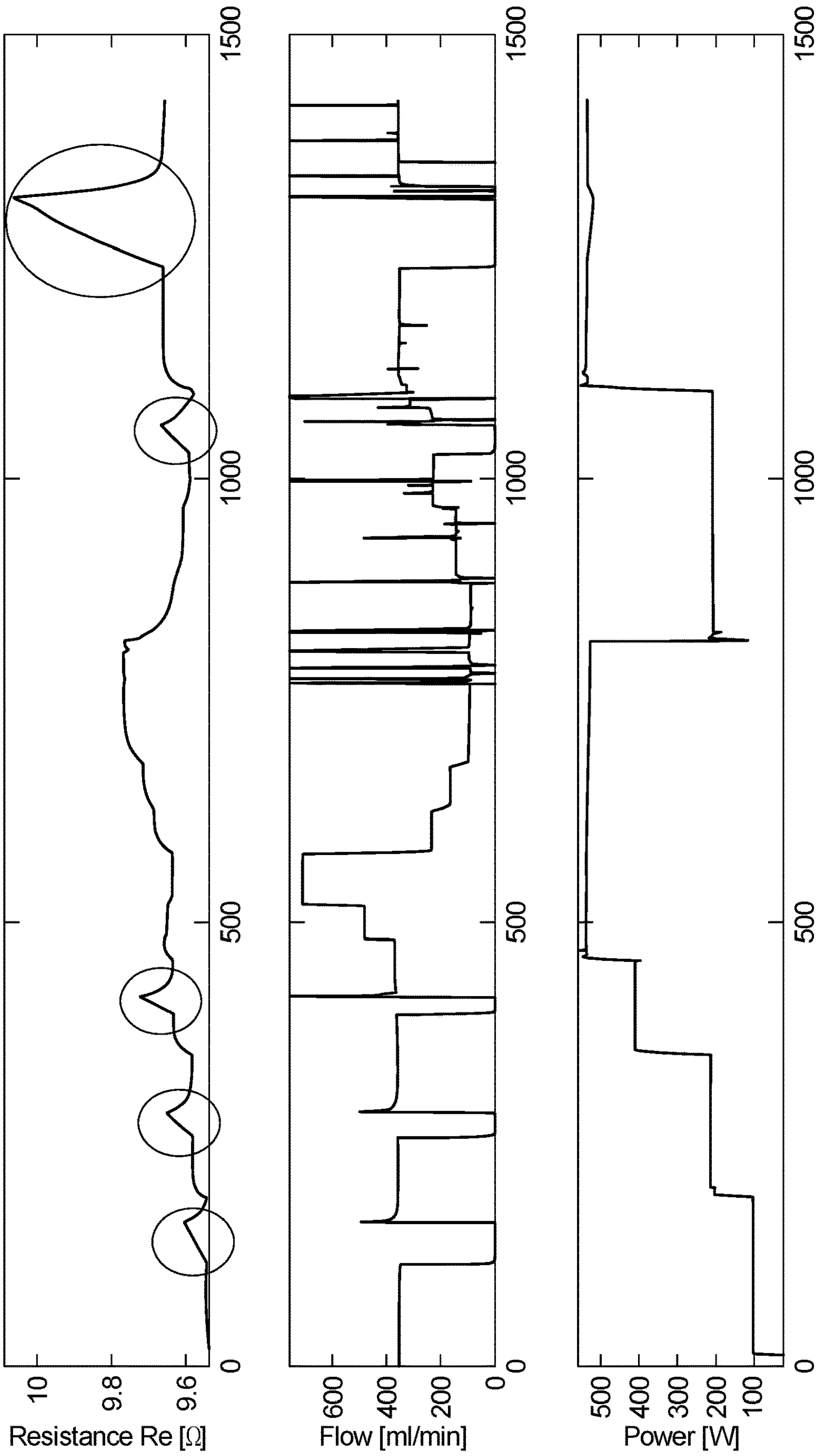
FIG. 4 is a collection of graphs correlating inline heater power input, dialysis fluid flowrate and heater element resistance over a common time period.

Referring now to FIG. 4, a collection of graphs over a common time period correlating inline heater power input applied to heater elements 26*a*, 26*b*, dialysis fluid flowrate through inline heater 20 and heater element resistance $R_e$ is illustrated. The graphs highlight for example that as power to heater elements 26*a*, 26*b* increases, e.g., from 100 Watts, to 200 Watts, to 300 Watts, heater element resistance $R_e$ increases in turn from about 9.52 Ohms, to about 9.6 Ohms, to about 9.66 Ohms, respectively, which coincides with an increase in heater element temperature. The graphs also highlight that whenever dialysis fluid or other fluid flowrate is stopped, while input power continues to be applied, heater element resistance $R_e$ increases sharply, which also coincides with a sharp increase in heater element temperature.

One possible algorithm stored in memory 54 and interrogated by processor 52 sets a maximum heater element resistance increase or resistance derivate (change in heater element resistance over time). With control unit analysing heater element resistance $R_e$ rate change or increase over time, a no or low flow condition through the inline heater 20 is detectable before the temperature of heater elements 26*a*, 26*b* increases to a point that could damage inline heater 20. When there is no fluid flow in an energized inline heater 20, the temperature of heater elements 26*a*, 26 increases rapidly and hence the heater element resistance $R_e$ increases rapidly. Control unit 50 is accordingly programmed to look to determine if a change in heater element resistance $R_e$ over a period or of time (rate of change), e.g., to determine if a sample period rate of change of resistance $R_e$ meets or exceeds a set maximum rate of change of resistance $R_e$ over the period of time, the algorithm triggers control unit 50 to automatically deenergize inline heater 20, stop treatment at the corresponding machine or cycler (or stop preparing purified water or stop preparing dialysis fluid at the corresponding unit), and alarm the patient, caregiver or nurse, e.g., at user interface 60.

One possible implementation of the overheating algorithm of inline heating system 10 is to run a characterizing program that characterizes inline heater 20 at the time of manufacture and/or servicing of the dialysis machine (or other unit). The characterizing program characterises how heater element resistance $R_e$ relates to input power and flowrate. Here, the inline heater is energized while receiving a known flowrate of fluid. Input power is varied while the flowrate is held constant. Temperature sensor 18*t* may be used to measure the test fluid temperature downstream form inline heater 20 to confirm that the inline heater is heating the test fluid properly to the commanded temperature. The output of pump 16 is monitored to confirm that the commanded flowrate is met (a weight scale may be used in the test setting). The characterising program enables measured heater element resistances $R_e$ (correlated with heater element temperature) for the particular inline heater 20 tested to be known for a commanded flowrate and fluid temperature, and over a common or use range of input power settings. A resulting calibration data table is then stored in memory 54 of control unit 50 of the dialysis machine (or other unit). Control unit 50 uses the calibration data during treatment to detect when inline heater 20 is overheating, that is, to detect that for a given or commanded flowrate and input power setting to achieve a commanded temperature, whether a measured and determined heater element resistance $R_e$ is greater than it should be for the commanded dialysis fluid temperature.

The algorithm stored in memory 54 of control unit 50 of the dialysis machine (or other unit) may accordingly analyze two factors (i) rate of change in heater element resistance (derivative) indicating that a no or low flow condition may be beginning and (ii) a comparison between a determined heater element resistance $R_e$ to the calibration resistance for the same input power and commanded flowrate. That is, the rate of change in heater element resistance $R_e$ may be high, indicating that a no or low flow condition may be underway, but if the determined heater element resistance (and corresponding temperature) is lower than what the calibration data says the heater element resistance should be for a given flowrate and power input setting, then the algorithm allows control unit 50 of dialysis machine (or other unit) to continue treatment.

In an embodiment, the cycle rate for the current or voltage measurement to determine heater element resistance $R_e$ may be very high, and thus the algorithm may be configured to take many measurements, e.g., over the period of a second or more, before making a no or low flow determination, deenergizing inline heater 20, stopping treatment, and alarming the patient, caregiver or nurse. Taking many measurements over a safe time period that is too short for inline heater 20 to overheat significantly helps to prevent false trips.

Taking many measurements also provides an adequate number of samples to efficiently supress measurement signal noise. The measurement signal for heater element resistance $R_e$ tends to be very noisy due to its environment including a pulsed power source. In one implementation, the high sampling rate was 5 kHz, and a multi- or four step decimation procedure was applied. Each decimation step was performed by applying an 8th order Chebyshev lowpass filter type I and by removing samples to a 10th of a fraction of the original or prior step, e.g., to 500 samples, then 50 samples, etc. There are numerous ways of performing the filtering leading to the heater element resistance $R_e$ graph at the top of FIG. 4. It is likely, however, that successful filtering requires a large sample rate, such as 5 kHz. The sample rate will depend on the frequency of the pulsed voltage source, e.g., if a typical 50/60 Hz AC voltage source, a sample rate of at least two times as fast, e.g., 100 to 120 Hz is likely required. However, the sample rate may desirably be at least ten times higher, e.g., 500 to 600 Hz.

It should be understood that various changes and modifications to the presently preferred embodiments described herein will be apparent to those skilled in the art. It is therefore intended that any or all of such changes and modifications may be covered by the appended claims. For example, while inline heating system 10 is shown interrogating two heater elements 26*a*, 26*b* (e.g., for redundancy where a rise in resistance at either element can trip a no or low flow outcome), the inline heating systems of the present disclosure may instead interrogate only a single or less than all of the heater elements of inline heater 20.

The invention is claimed as follows:

1. An inline heating system comprising:

an inline heater including a heater element;

a control unit configured to cause one of a voltage or a current to be applied to power the inline heater;

a memory communicatively coupled to the control unit, the memory configured to store a calibration data table that relates calibrated heater element resistances of the inline heater to at least one of fluid flowrates through the inline heater or input voltages or currents to the inline heater; and at least one meter arranged to measure at least one of a current or voltage at the heater element due to the applied voltage or the applied current, the at least one meter outputting the at least one of the current or the voltage to the control unit, wherein the control unit is further configured to:

determine a heater element resistance (Re) of the inline heater using the applied voltage or the applied current and the measured at least one of the current or the voltage as part of a no flow or low flow condition detection algorithm implemented by the control unit, compare the determined heater element resistance (Re) of the inline heater with a commanded fluid flowrate and a power setting of the heater element to the calibration data table to determine whether a no flow or low flow condition is detected, and stop applying the voltage or the current to power the inline heater upon detection of the no flow or low flow condition.

2. The inline heating system of claim 1, wherein the control unit includes the at least one meter.

3. The inline heating system of claim 1, wherein the control unit is configured to determine multiple heater element resistances using the applied voltage or the applied current and the measured at least one current or voltage at different times over a sample period to determine if the no flow or low flow condition is detected.

4. The inline heating system of claim 1, further comprising at least one additional heater element, wherein the control unit is configured to determine a heater element resistance for each of the at least one additional heater element as part of the no flow or low flow condition detection algorithm.

5. The inline heating system of claim 4, further comprising at least one additional meter arranged to measure the at least one current or voltage at the at least one additional heater element.

6. The inline heating system of claim 4, wherein the control unit is configured to stop the voltage or the current applied to power the inline heater if the no flow or low flow condition is detected at any of the heater elements.

7. The inline heating system of claim 1, wherein the control unit is configured to compare a rate of change in the determined heater element resistance to a et maximum rate of change in the determined heater element resistance as part of the low flow condition detection algorithm implemented by the control unit.

8. The inline heating system of claim 7, wherein the rate of change in the determined heater element resistance is a positive rate of change.

9. The inline heating system of claim 1, wherein the calibrated heater element resistances are determined remotely from the inline heating system and then stored in the control unit.

10. The inline heating system of claim 1, wherein the control unit is configured to determine the at least one of the current or the voltage at a sample rate that is of at least one of (i) 100 Hz or greater, or (ii) at least two times greater than a frequency of a pulsed voltage source powering the inline heater.

11. The inline heating system of claim 1, wherein the control unit includes an analog heater protection circuit configured to filter the measured at least one of the current or the voltage.

12. An inline heating system comprising:

an inline heater including a heater element;

a voltage source or a current source positioned to apply a voltage or a current to power the inline heater a memory configured to store a calibration data table that relates calibrated heater element resistances of the inline heater to at least one of fluid flowrates through the inline heater or input voltages or input currents to the inline heater; and an analog heater protection circuit configured to:

(i) measure at least one of a current or a voltage at the heater element due to the applied voltage or the applied current, (ii) determine a heater element resistance (Re) of the inline heater using the applied voltage or the applied current and the measured at least one of the current or the voltage, (iii) compare the determined heater element resistance (Re) of the inline heater with a commanded fluid flowrate and a power setting of the heater element to the calibration data table to determine whether a no flow or low flow condition is detected, and (iv) (iv) stop a power signal or disable an enable signal when the heater element resistance of the inline heater indicates the no flow or low flow condition.

13. The inline heating system of claim 12, wherein the analog heater protection circuit includes at least one of: a measurement circuit, a divider circuit, a differential circuit, or a comparator.

14. An inline heating system comprising:

an inline heater including a heater element;

a control unit configured to: compare a determined heater element resistance (Re) of the inline heater with a commanded fluid flowrate and a power setting of the inline heater to a calibration data table to determine whether a no flow or low flow condition is detected, and stop applying a current or a voltage to power the inline heater upon detection of the no flow or low flow condition; and a meter arranged to measure at least one of a current or a voltage at the heater element due to the applied voltage or the applied current, the meter outputting the at least one of the current or the voltage to the control unit to enable the control unit to calibrate the determined resistance to the outputted at least one of the current or voltage.

15. The inline heating system of claim 14, wherein the inline heating system is provided as part of a peritoneal dialysis machine, a hemodialysis machine, a hemofiltration machine, a hemodiafiltration machine, a continuous renal replacement therapy machine, a water purification unit, a dialysis fluid preparation unit, or a blood warmer.

* * * * *